United States Patent
Zhu et al.

(10) Patent No.: US 6,723,546 B2
(45) Date of Patent: Apr. 20, 2004

(54) **METHOD FOR CLONING AND EXPRESSION OF BSAI RESTRICTION ENDONUCLEASE AND BSAI METHYLASE IN *E. COLI***

(75) Inventors: Zhenyu Zhu, Beverly, MA (US); Shuang-Yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 35 days.

(21) Appl. No.: 10/106,275

(22) Filed: Mar. 26, 2002

(65) Prior Publication Data

US 2003/0186363 A1 Oct. 2, 2003

(51) Int. Cl.[7] ............................ C12N 9/22; C12N 15/55
(52) U.S. Cl. .............. 435/194; 435/320.1; 435/252.33; 536/23.2
(58) Field of Search .................... 435/199, 320.1, 435/252.33; 536/23.2

(56) References Cited

U.S. PATENT DOCUMENTS

| | | | |
|---|---|---|---|
| 5,200,333 A | 4/1993 | Wilson | 435/172.3 |
| 5,498,535 A | 3/1996 | Fomenkov et al. | 435/172.3 |

OTHER PUBLICATIONS

Roberts and Macelis, Nucl. Acids Res. 29:268–269 (2001).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Walder et al., J. Biol. Chem. 258: 1235–1241, (1983).
Fomenkov et al., Nucl. Acids Res. 22: 2399–2403, (1994).
Malone et al., J. Mol. Biol. 253: 618–632, (1995).
New England Biolabs' Catalog, 2000–01, p. 220.
Kong, et al., Nucl. Acids. Res. 28:3216–3223 (2000).
Rebase, New England Biolabs, USA, Roberts, et al., "BsaI", Rebase enzyme #313.
Rebase, New England Biolabs, USA, Roberts, et al., "M.BsaIA", Rebase enzyme #5671.
Rebase, New England Biolabs, USA, Roberts, et al., "M.BsaIB", Rebase enzyme #4777.

*Primary Examiner*—Charles L. Patterson, Jr.
(74) *Attorney, Agent, or Firm*—Gregory D. Williams

(57) ABSTRACT

The present invention relates to recombinant DNA which encodes the BsaI restriction endonuclease as well as BsaI methylase, expression of BsaI restriction endonuclease and BsaI methylase in *E. coli* cells containing the recombinant DNA, and purification of BsaI restriction endonuclease to near homogeneity.

6 Claims, 8 Drawing Sheets

FIG. 2A

```
      TTGAGTAATGCTAAAAGTTTCTCTCTTAACGAAAAAACAGAAGCTAATGCTCTAATAGAT
   1----------+---------+---------+---------+---------+---------+60
       M  S  N  A  K  S  F  S  L  N  E  K  T  E  A  N  A  L  I  D
      TTTATTATTGAAAAATCTAATCAAAGTAAAGACTTGGGTTATTGGTTACAAAAATCAAAA
  61----------+---------+---------+---------+---------+---------+120
       F  I  I  E  K  S  N  Q  S  K  D  L  G  Y  W  L  Q  K  S  K
      GGACAGTTTTATACACATAATTTTATTGGTGAAAAATTAGTTACAGAAATAGTAGAAAAT
 121----------+---------+---------+---------+---------+---------+180
       G  Q  F  Y  T  H  N  F  I  G  E  K  L  V  T  E  I  V  E  N
      ATAAAATTTAATGATGATAGTGAAGTTATAAAAATAATTGACCCTTTTTGTGGAGATGGA
 181----------+---------+---------+---------+---------+---------+240
       I  K  F  N  D  D  S  E  V  I  K  I  I  D  P  F  C  G  D  G
      CGCTTAATATGCATTTTGTTAGATAAATTTAATGCTATAAATAAATTTAGAAATACCTTG
 241----------+---------+---------+---------+---------+---------+300
       R  L  I  C  I  L  L  D  K  F  N  A  I  N  K  F  R  N  T  L
      TTAGAGATTGAATTTTGGGATATTGACCCTGAAGCTGTAGAAGTTGCTTATACCAATATA
 301----------+---------+---------+---------+---------+---------+360
       L  E  I  E  F  W  D  I  D  P  E  A  V  E  V  A  Y  T  N  I
      AAAGAGAAAGCTAATGCATTAGAATTTAATGTACAACTAAAGGGGAGAGTATGCGATACT
 361----------+---------+---------+---------+---------+---------+420
       K  E  K  A  N  A  L  E  F  N  V  Q  L  K  G  R  V  C  D  T
      TTTCTTTTTGCTCAAGACTACTTTGGCTCATATGATATCTGTATTACAAACCCGCCATGG
 421----------+---------+---------+---------+---------+---------+480
       F  L  F  A  Q  D  Y  F  G  S  Y  D  I  C  I  T  N  P  P  W
      GTAATTATAAAACCAGATAAAAAGGAAAAGGAAAGGTTAAGTAAAGAAGAAGAGATAGAG
 481----------+---------+---------+---------+---------+---------+540
       V  I  I  K  P  D  K  K  E  K  E  R  L  S  K  E  E  E  I  E
      TATATTGAAATACTAAAGAATTTTGATGATTTTTTGAGTAGATACTATCCTACTTCTTTA
 541----------+---------+---------+---------+---------+---------+600
       Y  I  E  I  L  K  N  F  D  D  F  L  S  R  Y  Y  P  T  S  L
      CCTACAAAAAAATATGGAGGATGGGGAACTAACTTAGCTAGATGTGGTACAGAAGTTGCG
 601----------+---------+---------+---------+---------+---------+660
       P  T  K  K  Y  G  G  W  G  T  N  L  A  R  C  G  T  E  V  A
      CTGAGATTAATTTCAAAAGTAGGGATTTGTGGTATAGTATCACCAGCATCGCTTTTAGGT
 661----------+---------+---------+---------+---------+---------+720
       L  R  L  I  S  K  V  G  I  C  G  I  V  S  P  A  S  L  L  G
      GACCAAGTATCGGATAATCTTAGAGTTTGGATGTTTAATAACTATGAGGTTTATAGTATT
 721----------+---------+---------+---------+---------+---------+780
       D  Q  V  S  D  N  L  R  V  W  M  F  N  N  Y  E  V  Y  S  I
      TCTTACTTTGTTGCAGAAGCTAAATTATTTGGTAAAGTAGACCAAGCAGTTATTACATTA
 781----------+---------+---------+---------+---------+---------+840
       S  Y  F  V  A  E  A  K  L  F  G  K  V  D  Q  A  V  I  T  L
      ACTTTATCACCTAAATGTGATGATAGTAGTGGTGATATTATTCCGCATCTGTTTTACTAC
 841----------+---------+---------+---------+---------+---------+900
       T  L  S  P  K  C  D  D  S  S  G  D  I  I  P  H  L  F  Y  Y
      GATAGAGAGCTATTTGAAAAAAGATATTATATGGATGAATATGATTGGCGTATTATAAAG
 901----------+---------+---------+---------+---------+---------+960
       D  R  E  L  F  E  K  R  Y  Y  M  D  E  Y  D  W  R  I  I  K
      TCACTCAATTATGTTATTCCAATTCAATTTGGTTTAGAGATAATAAAAATGAATAGATTA
 961----------+---------+---------+---------+---------+---------+1020
       S  L  N  Y  V  I  P  I  Q  F  G  L  E  I  I  K  M  N  R  L
      TTTAAGTCTTTACCCACTTTAGGGGACTTAGAGAACGAAAAAGAAGGGATTTGGCTAGGA
1021----------+---------+---------+---------+---------+---------+1080
       F  K  S  L  P  T  L  G  D  L  E  N  E  K  E  G  I  W  L  G
```

FIG. 2B

```
     AGGGAACTAGATGAAACCGGAATAAAGGAAAAATTGGCTAACAAAGGTCAATATCGTTTT
1081 ------------+---------+---------+---------+---------+---------+1140
      R  E  L  D  E  T  G  I  K  E  K  L  A  N  K  G  Q  Y  R  F
     ATCAAAGGGAAAATGGTAGGAAGATACAACCTAATTGAAGAGTCTAATCAATATATTGAT
1141 ------------+---------+---------+---------+---------+---------+1200
      I  K  G  K  M  V  G  R  Y  N  L  I  E  E  S  N  Q  Y  I  D
     GTTAGAAAGATAGATAAAATCCCCAAATCTGTCGAATTTTACAGATTGGTCTGGAGAGAT
1201 ------------+---------+---------+---------+---------+---------+1260
      V  R  K  I  D  K  I  P  K  S  V  E  F  Y  R  L  V  W  R  D
     GTCTCAAGAACGACTCAAAAAAGAAGATTAATATCAACAATTATTCCACCTAAATATATT
1261 ------------+---------+---------+---------+---------+---------+1320
      V  S  R  T  T  Q  K  R  R  L  I  S  T  I  I  P  P  K  Y  I
     ACTGGCAATTCACTTAATGTAGCTTATTTCAAAGATAATAATTTAAAGAAATTAAAAGCT
1321 ------------+---------+---------+---------+---------+---------+1380
      T  G  N  S  L  N  V  A  Y  F  K  D  N  N  L  K  K  L  K  A
     TTACTTGCAATCATGAATTCATTTGTTTTTGAAGCTCAAGTAAGAGCTAATTTATCTACA
1381 ------------+---------+---------+---------+---------+---------+1440
      L  L  A  I  M  N  S  F  V  F  E  A  Q  V  R  A  N  L  S  T
     AATCATATTTCTTTGGGAATAATAAGGAGAGCACATATACCGAAGTTAGAAGGTAGAGTT
1441 ------------+---------+---------+---------+---------+---------+1500
      N  H  I  S  L  G  I  I  R  R  A  H  I  P  K  L  E  G  R  V
     GTGGATGAACTTTCTCAACTAGTTGATAATTATGTTAATGAAGAAAGCGAATTACTATTA
1501 ------------+---------+---------+---------+---------+---------+1560
      V  D  E  L  S  Q  L  V  D  N  Y  V  N  E  E  S  E  L  L  L
     GAAGTAAAAGTTGCTAAAGCATATGGACTCTCATTTGAAGATTTTAGTTCAATTCTTTCT
1561 ------------+---------+---------+---------+---------+---------+1620
      E  V  K  V  A  K  A  Y  G  L  S  F  E  D  F  S  S  I  L  S
     CTATTTGACAAGATAGGTAAAGACGAAAAAGAAAAGATACTACAAGTAGCAAAAAAATAT
1621 ------------+---------+---------+---------+---------+---------+1680
      L  F  D  K  I  G  K  D  E  K  E  K  I  L  Q  V  A  K  K  Y
     TTAAAGGGGGGAATAAAGAATGATTCCTAA
1681 ------------+---------+---------+1710
      L  K  G  G  I  K  N  D  S  *
```

FIG. 3A

```
     ATGATTCCTAATCATGTTTCATCAAAATTAAGTGAACTTGATATGTTAATCATTAAGCAT
   1 ------------------------------------------------------------ 60
      M  I  P  N  H  V  S  S  K  L  S  E  L  D  M  L  I  I  K  H
     GTACCTCCAGGAGGTAATTGGAAGGACATTCCAGAATGGGTTCCTTCTAAAAGATTAGAA
  61 ------------------------------------------------------------ 120
      V  P  P  G  G  N  W  K  D  I  P  E  W  V  P  S  K  R  L  E
     CAAATACGAAAAAGTTATGCAGAAGGAAAGGGAAGTCGTTCTACGTATTATGGTAGACTT
 121 ------------------------------------------------------------ 180
      Q  I  R  K  S  Y  A  E  G  K  G  S  R  S  T  Y  Y  G  R  L
     CTTCCAGATATGCCTTCTTATACAATAAACACTTATTTTAATAGACCAGGAAATGGTTGT
 181 ------------------------------------------------------------ 240
      L  P  D  M  P  S  Y  T  I  N  T  Y  F  N  R  P  G  N  G  C
     CATATACATTATGAGCAAGATAGGACATTATCTCAACGTGAGGCAGCTAGACTTCAGTCA
 241 ------------------------------------------------------------ 300
      H  I  H  Y  E  Q  D  R  T  L  S  Q  R  E  A  A  R  L  Q  S
     TTTCCTGATGATTTTATTTTTTATGGAAGTAAAACAGCCATAAATAATCAGATTGGAAAT
 301 ------------------------------------------------------------ 360
      F  P  D  D  F  I  F  Y  G  S  K  T  A  I  N  N  Q  I  G  N
     GCAGTACCGCCGTTATTAGCGTATCAAATAGCTAAAGCATTTCCCTTTAAAGGACAATTT
 361 ------------------------------------------------------------ 420
      A  V  P  P  L  L  A  Y  Q  I  A  K  A  F  P  F  K  G  Q  F
     GTCGACTTGTTTAGTGGTGCAGGAGGTCTTTCTCTAGGATTTTTATGGGCAGGTTGGAAA
 421 ------------------------------------------------------------ 480
      V  D  L  F  S  G  A  G  G  L  S  L  G  F  L  W  A  G  W  K
     CCTATAATTGCAAATGATATTGATAAATGGGCACTAACAACTTACATGAATAACATACAT
 481 ------------------------------------------------------------ 540
      P  I  I  A  N  D  I  D  K  W  A  L  T  T  Y  M  N  N  I  H
     AATGAAGTTGTTTTAGGGGATATAAGAGATGAAAAAGTATCAGAAACAATCATTCAAAAA
 541 ------------------------------------------------------------ 600
      N  E  V  V  L  G  D  I  R  D  E  K  V  S  E  T  I  I  Q  K
     TGCCTAATAGCAAAGAAAAGCAATCCAGATAGACCATTGTTTGTTTTAGGTGGACCACCT
 601 ------------------------------------------------------------ 660
      C  L  I  A  K  K  S  N  P  D  R  P  L  F  V  L  G  G  P  P
     TGTCAAGGTTTTTCTACTGCTGGAAAAAAGCGTAGCATAGTAGATGAAAGAAACTGGCTT
 661 ------------------------------------------------------------ 720
      C  Q  G  F  S  T  A  G  K  K  R  S  I  V  D  E  R  N  W  L
     TTTGAATCTTACGTATCAATATTAAAAGAAGTTAAACCAGATGGATTTATTTTTGAAAAT
 721 ------------------------------------------------------------ 780
      F  E  S  Y  V  S  I  L  K  E  V  K  P  D  G  F  I  F  E  N
     GTAACAGGTTTATTAAGTATGGAAAAAGGTGCGTTTTTTGAAATGGTTAAGTCAGAATTA
 781 ------------------------------------------------------------ 840
      V  T  G  L  L  S  M  E  K  G  A  F  F  E  M  V  K  S  E  L
     AGTAAAACAGTTTCTAACCTATTTGTATATAAACTAAATAGTGTAGATTATGGGGTTCCT
 841 ------------------------------------------------------------ 900
      S  K  T  V  S  N  L  F  V  Y  K  L  N  S  V  D  Y  G  V  P
     CAGAGAAGAAATAGGGTAGTAATCATAGGTGACTCAACGGGTACTAAAAACAGTGAACCA
 901 ------------------------------------------------------------ 960
      Q  R  R  N  R  V  V  I  I  G  D  S  T  G  T  K  N  S  E  P
     CCAATTCCTATTACATCTCTAAAAGGTGAGAAAACATTATTTGATGCCCTTTCATCAGCC
 961 ------------------------------------------------------------ 1020
      P  I  P  I  T  S  L  K  G  E  K  T  L  F  D  A  L  S  S  A
     ATATCAGTAAAAGAAGCTTTATCTGATTTACCATTGCTTTCTCCTAATGAAGATGGCTCT
1021 ------------------------------------------------------------ 1080
      I  S  V  K  E  A  L  S  D  L  P  L  L  S  P  N  E  D  G  S
```

FIG. 3B

```
     TGGAAAAATTATGTTTGTGAGCCACAGAATATCTATCAAAGTTTTATGAGGAAAAAGATT
1081 ------------+----------+----------+----------+----------+----------+ 1140
     W  K  N  Y  V  C  E  P  Q  N  I  Y  Q  S  F  M  R  K  K  I
     ACTGCTCAACAATATATAGAAATGTTGAGCAGTTTAGCGATAATATAA
1141 ------------+----------+----------+----------+-------- 1188
     T  A  Q  Q  Y  I  E  M  L  S  S  L  A  I  I  *
```

FIG. 4A

```
    TTGGGAAAAAAAGCTGAATATGGACAGGGACATCCAATATTTTTAGAATATGCTGAACAG
  1---------+---------+---------+---------+---------+---------+60
    M G K K A E Y G Q G H P I F L E Y A E Q
    ATAATCCAACATAAAGAATACCAAGGTATGCCAGACTTAAGATACCCTGATGGAAGAATT
 61---------+---------+---------+---------+---------+---------+120
    I I Q H K E Y Q G M P D L R Y P D G R I
    CAGTGGGAAGCACCTTCAAATAGAAAAAGCGGTATATTTAAAGACACTAACATTAAGCGA
121---------+---------+---------+---------+---------+---------+180
    Q W E A P S N R K S G I F K D T N I K R
    AGAAAATGGTGGGAACAAAAAGCTATTTCTATCGGGATAGACCCTTCTAGTAATCAATGG
181---------+---------+---------+---------+---------+---------+240
    R K W W E Q K A I S I G I D P S S N Q W
    ATTAGTAAGACAGCCAAATTAATTCATCCAACAATGAGAAAACCTTGCAAAAAGTGCGGA
241---------+---------+---------+---------+---------+---------+300
    I S K T A K L I H P T M R K P C K K C G
    AGGATAATGGATTTACGATATAGCTATCCTACCAAAAATCTTATTAAACGCATTAGAAAA
301---------+---------+---------+---------+---------+---------+360
    R I M D L R Y S Y P T K N L I K R I R K
    TTACCTTATGTTGATGAATCGTTTGAAATTGATTCACTAGAACATATTTTAAAACTTATT
361---------+---------+---------+---------+---------+---------+420
    L P Y V D E S F E I D S L E H I L K L I
    AAACGTTTAGTTCTACAATATGGTGATAAAGTATACGATGATTTGCCTAAACTACTAACT
421---------+---------+---------+---------+---------+---------+480
    K R L V L Q Y G D K V Y D D L P K L L T
    TGCAAAGCAGTTAAAAATATTCCAAGATTGGGAAACGATTTAGATACTTGGTTAAATTGG
481---------+---------+---------+---------+---------+---------+540
    C K A V K N I P R L G N D L D T W L N W
    ATTGATTCTGTTTATATTCCGAGTGAACCTAGTATGCTTAGTCCAGGCGCTATGGCAAAT
541---------+---------+---------+---------+---------+---------+600
    I D S V Y I P S E P S M L S P G A M A N
    CCGCCAGATAGATTAGATGGGTTCCACTCATTAAATGAATGCTGTAGAAGTCATGCTGAT
601---------+---------+---------+---------+---------+---------+660
    P P D R L D G F H S L N E C C R S H A D
    AGAGGTAGATGGGAAAAAAACCTGCGGTCATATACAACAGATAGAAGAGCATTTGAATAC
661---------+---------+---------+---------+---------+---------+720
    R G R W E K N L R S Y T T D R R A F E Y
    TGGGTTGATGGAGATTGGGTTGCAGCTGACAAACTTATGGGACTAATAAGAACAAATGAA
721---------+---------+---------+---------+---------+---------+780
    W V D G D W V A A D K L M G L I R T N E
    CAGATAAAGAAGGAAACTTGTTTAAATGATAACCACCCAGGCCCTTGTTCTGCAGACCAT
781---------+---------+---------+---------+---------+---------+840
    Q I K K E T C L N D N H P G P C S A D H
    ATTGGTCCTATTTCCCTTGGTTTTGTTCACAGGCCAGAGTTTCAATTGCTATGTAACTCA
841---------+---------+---------+---------+---------+---------+900
    I G P I S L G F V H R P E F Q L L C N S
    TGTAACAGTGCCAAAAATAATCGAATGACTTTTTCAGATGTCCAACACTTAATTAATGCG
901---------+---------+---------+---------+---------+---------+960
    C N S A K N N R M T F S D V Q H L I N A
    GAAAATAATGGAGAAGAGGTTGCATCTTGGTACTGTAAACATATATGGGATTTAAGAAAA
961---------+---------+---------+---------+---------+---------+1020
    E N N G E E V A S W Y C K H I W D L R K
    CATGATGTTAAAAAACAACGAAAACGCATTGAGATTAAGTAAAATTTTAAGAGATAATCGC
1021---------+---------+---------+---------+---------+---------+1080
    H D V K N N E N A L R L S K I L R D N R
```

FIG. 4B

```
     CATACAGCTATGTTTATATTAAGTGAGTTATTAAAAGATAATCACTATCTTTTCCTTTCA
1081 ------------+---------+---------+---------+---------+---------+ 1140
      H T A M F I L S E L L K D N H Y L F L S
     ACTTTTTTAGGATTACAGTATGCAGAAAGGTCTGTAAGTTTTTCAAATATAAAAATTGAA
1141 ------------+---------+---------+---------+---------+---------+ 1200
       T F L G L Q Y A E R S V S F S N I K I E
     AATCATATTATCACAGGACAAATTTCTGAACAACCAAGAGATACAAAATACACTGAAGAG
1201 ------------+---------+---------+---------+---------+---------+ 1260
      N H I I T G Q I S E Q P R D T K Y T E E
     CAAAAAGCCAGAAGAATGAGAATTGGATTCGAAGCACTTAAAAGCTATATTGAAAAAGAA
1261 ------------+---------+---------+---------+---------+---------+ 1320
      Q K A R R M R I G F E A L K S Y I E K E
     AACAGAAATGCCTTATTAGTAATAAATGATAAAATTATTGATAAAATTAACGAAATAAAA
1321 ------------+---------+---------+---------+---------+---------+ 1380
      N R N A L L V I N D K I I D K I N E I K
     AATATATTACAAGATATTCCAGACGAATATAAACTTTTAAATGAAAAAATCTCTGAGCAA
1381 ------------+---------+---------+---------+---------+---------+ 1440
      N I L Q D I P D E Y K L L N E K I S E Q
     TTCAACAGTGAAGAAGTTTCTGATGAACTACTCAGAGATTTAGTTACTCATCTCCCAACT
1441 ------------+---------+---------+---------+---------+---------+ 1500
      F N S E E V S D E L L R D L V T H L P T
     AAAGAAAGTGAACCAGCTAACTTTAAATTGGCTAGAAAATACTTGCAAGAAATAATGGAA
1501 ------------+---------+---------+---------+---------+---------+ 1560
      K E S E P A N F K L A R K Y L Q E I M E
     ATAGTAGGAGATGAACTTTCAAAAATGTGGGAAGATGAACGATACGTAAGACAAACATTT
1561 ------------+---------+---------+---------+---------+---------+ 1620
      I V G D E L S K M W E D E R Y V R Q T F
     GCAGATTTAGATTAA
1621 ------------+----- 1635
      A D L D *
```

SEQUENCE LISTING

<160> NUMBER OF SEQ ID NOS: 23

<210> SEQ ID NO 1
<211> LENGTH: 1710
<212> TYPE: DNA
<213> ORGANISM: Bacillus stearothermophilus 6-55
<220> FEATURE:
<221> NAME/KEY: CDS
<222> LOCATION: (1)..(1710)
<223> OTHER INFORMATION:

<400> SEQUENCE: 1

```
ttg agt aat gct aaa agt ttc tct ctt aac gaa aaa aca gaa gct aat        48
Leu Ser Asn Ala Lys Ser Phe Ser Leu Asn Glu Lys Thr Glu Ala Asn
1               5                   10                  15 gct cta ata gat ttt att att gaa aaa tct aat caa agt aaa gac ttg        96
Ala Leu Ile Asp Phe Ile Ile Glu Lys Ser Asn Gln Ser Lys Asp Leu
                20                  25                  30 ggt tat tgg tta caa aaa tca aaa gga cag ttt tat aca cat aat ttt       144
Gly Tyr Trp Leu Gln Lys Ser Lys Gly Gln Phe Tyr Thr His Asn Phe
            35                  40                  45 att ggt gaa aaa tta gtt aca gaa ata gta gaa aat ata aaa ttt aat       192
Ile Gly Glu Lys Leu Val Thr Glu Ile Val Glu Asn Ile Lys Phe Asn
        50                  55                  60 gat gat agt gaa gtt ata aaa ata att gac cct ttt tgt gga gat gga       240
Asp Asp Ser Glu Val Ile Lys Ile Ile Asp Pro Phe Cys Gly Asp Gly
65                  70                  75                  80
```

-continued

| | |
|---|---|
| cgc tta ata tgc att ttg tta gat aaa ttt aat gct ata aat aaa ttt<br>Arg Leu Ile Cys Ile Leu Leu Asp Lys Phe Asn Ala Ile Asn Lys Phe<br>                          85                      90                      95 | 288 |
| aga aat acc ttg tta gag att gaa ttt tgg gat att gac cct gaa gct<br>Arg Asn Thr Leu Leu Glu Ile Glu Phe Trp Asp Ile Asp Pro Glu Ala<br>                 100                     105                     110 | 336 |
| gta gaa gtt gct tat acc aat ata aaa gag aaa gct aat gca tta gaa<br>Val Glu Val Ala Tyr Thr Asn Ile Lys Glu Lys Ala Asn Ala Leu Glu<br>             115                     120                     125 | 384 |
| ttt aat gta caa cta aag ggg aga gta tgc gat act ttt ctt ttt gct<br>Phe Asn Val Gln Leu Lys Gly Arg Val Cys Asp Thr Phe Leu Phe Ala<br>130                     135                     140 | 432 |
| caa gac tac ttt ggc tca tat gat atc tgt att aca aac ccg cca tgg<br>Gln Asp Tyr Phe Gly Ser Tyr Asp Ile Cys Ile Thr Asn Pro Pro Trp<br>145                     150                     155                     160 | 480 |
| gta att ata aaa cca gat aaa aag gaa aag gaa agg tta agt aaa gaa<br>Val Ile Ile Lys Pro Asp Lys Lys Glu Lys Glu Arg Leu Ser Lys Glu<br>                 165                     170                     175 | 528 |
| gaa gag ata gag tat att gaa ata cta aag aat ttt gat gat ttt ttg<br>Glu Glu Ile Glu Tyr Ile Glu Ile Leu Lys Asn Phe Asp Asp Phe Leu<br>             180                     185                     190 | 576 |
| agt aga tac tat cct act tct tta cct aca aaa aaa tat gga gga tgg<br>Ser Arg Tyr Tyr Pro Thr Ser Leu Pro Thr Lys Lys Tyr Gly Gly Trp<br>                 195                     200                     205 | 624 |
| gga act aac tta gct aga tgt ggt aca gaa gtt gcg ctg aga tta att<br>Gly Thr Asn Leu Ala Arg Cys Gly Thr Glu Val Ala Leu Arg Leu Ile<br>210                     215                     220 | 672 |
| tca aaa gta ggg att tgt ggt ata gta tca cca gca tcg ctt tta ggt<br>Ser Lys Val Gly Ile Cys Gly Ile Val Ser Pro Ala Ser Leu Leu Gly<br>225                     230                     235                     240 | 720 |
| gac caa gta tcg gat aat ctt aga gtt tgg atg ttt aat aac tat gag<br>Asp Gln Val Ser Asp Asn Leu Arg Val Trp Met Phe Asn Asn Tyr Glu<br>                 245                     250                     255 | 768 |
| gtt tat agt att tct tac ttt gtt gca gaa gct aaa tta ttt ggt aaa<br>Val Tyr Ser Ile Ser Tyr Phe Val Ala Glu Ala Lys Leu Phe Gly Lys<br>             260                     265                     270 | 816 |
| gta gac caa gca gtt att aca tta act tta tca cct aaa tgt gat gat<br>Val Asp Gln Ala Val Ile Thr Leu Thr Leu Ser Pro Lys Cys Asp Asp<br>             275                     280                     285 | 864 |
| agt agt ggt gat att att ccg cat ctg ttt tac tac gat aga gag cta<br>Ser Ser Gly Asp Ile Ile Pro His Leu Phe Tyr Tyr Asp Arg Glu Leu<br>290                     295                     300 | 912 |
| ttt gaa aaa aga tat tat atg gat gaa tat gat tgg cgt att ata aag<br>Phe Glu Lys Arg Tyr Tyr Met Asp Glu Tyr Asp Trp Arg Ile Ile Lys<br>305                     310                     315                     320 | 960 |
| tca ctc aat tat gtt att cca att caa ttt ggt tta gag ata ata aaa<br>Ser Leu Asn Tyr Val Ile Pro Ile Gln Phe Gly Leu Glu Ile Ile Lys<br>                 325                     330                     335 | 1008 |
| atg aat aga tta ttt aag tct tta ccc act tta ggg gac tta gag aac<br>Met Asn Arg Leu Phe Lys Ser Leu Pro Thr Leu Gly Asp Leu Glu Asn<br>             340                     345                     350 | 1056 |
| gaa aaa gaa ggg att tgg cta gga agg gaa cta gat gaa acc gga ata<br>Glu Lys Glu Gly Ile Trp Leu Gly Arg Glu Leu Asp Glu Thr Gly Ile<br>             355                     360                     365 | 1104 |
| aag gaa aaa ttg gct aac aaa ggt caa tat cgt ttt atc aaa ggg aaa<br>Lys Glu Lys Leu Ala Asn Lys Gly Gln Tyr Arg Phe Ile Lys Gly Lys<br>370                     375                     380 | 1152 |
| atg gta gga aga tac aac cta att gaa gag tct aat caa tat att gat<br>Met Val Gly Arg Tyr Asn Leu Ile Glu Glu Ser Asn Gln Tyr Ile Asp | 1200 |

```
                385                 390                 395                 400
gtt aga aag ata gat aaa atc ccc aaa tct gtc gaa ttt tac aga ttg       1248
Val Arg Lys Ile Asp Lys Ile Pro Lys Ser Val Glu Phe Tyr Arg Leu
                405                 410                 415 gtc tgg aga gat gtc tca aga acg act caa aaa aga aga tta ata tca       1296
Val Trp Arg Asp Val Ser Arg Thr Thr Gln Lys Arg Arg Leu Ile Ser
        420                 425                 430 aca att att cca cct aaa tat att act ggc aat tca ctt aat gta gct       1344
Thr Ile Ile Pro Pro Lys Tyr Ile Thr Gly Asn Ser Leu Asn Val Ala
            435                 440                 445 tat ttc aaa gat aat aat tta aag aaa tta aaa gct tta ctt gca atc       1392
Tyr Phe Lys Asp Asn Asn Leu Lys Lys Leu Lys Ala Leu Leu Ala Ile
        450                 455                 460 atg aat tca ttt gtt ttt gaa gct caa gta aga gct aat tta tct aca       1440
Met Asn Ser Phe Val Phe Glu Ala Gln Val Arg Ala Asn Leu Ser Thr
465                 470                 475                 480 aat cat att tct ttg gga ata ata agg aga gca cat ata ccg aag tta       1488
Asn His Ile Ser Leu Gly Ile Ile Arg Arg Ala His Ile Pro Lys Leu
                485                 490                 495 gaa ggt aga gtt gtg gat gaa ctt tct caa cta gtt gat aat tat gtt       1536
Glu Gly Arg Val Val Asp Glu Leu Ser Gln Leu Val Asp Asn Tyr Val
            500                 505                 510 aat gaa gaa agc gaa tta cta tta gaa gta aaa gtt gct aaa gca tat       1584
Asn Glu Glu Ser Glu Leu Leu Leu Glu Val Lys Val Ala Lys Ala Tyr
        515                 520                 525 gga ctc tca ttt gaa gat ttt agt tca att ctt tct cta ttt gac aag       1632
Gly Leu Ser Phe Glu Asp Phe Ser Ser Ile Leu Ser Leu Phe Asp Lys
    530                 535                 540 ata ggt aaa gac gaa aaa gaa aag ata cta caa gta gca aaa aaa tat       1680
Ile Gly Lys Asp Glu Lys Glu Lys Ile Leu Gln Val Ala Lys Lys Tyr
545                 550                 555                 560 tta aag ggg gga ata aag aat gat tcc taa                               1710
Leu Lys Gly Gly Ile Lys Asn Asp Ser
                565

<210> SEQ ID NO 2
<211> LENGTH: 569
<212> TYPE: PRT
<213> ORGANISM: Bacillus stearothermophilus 6-55

<400> SEQUENCE: 2

Leu Ser Asn Ala Lys Ser Phe Ser Leu Asn Glu Lys Thr Glu Ala Asn
1               5                   10                  15

Ala Leu Ile Asp Phe Ile Glu Lys Ser Asn Gln Ser Lys Asp Leu
            20                  25                  30

Gly Tyr Trp Leu Gln Lys Ser Lys Gly Gln Phe Tyr Thr His Asn Phe
        35                  40                  45

Ile Gly Glu Lys Leu Val Thr Glu Ile Val Glu Asn Ile Lys Phe Asn
    50                  55                  60

Asp Asp Ser Glu Val Ile Lys Ile Ile Asp Pro Phe Cys Gly Asp Gly
65                  70                  75                  80

Arg Leu Ile Cys Ile Leu Leu Asp Lys Phe Asn Ala Ile Asn Lys Phe
                85                  90                  95

Arg Asn Thr Leu Leu Glu Ile Glu Phe Trp Asp Ile Asp Pro Glu Ala
            100                 105                 110

Val Glu Val Ala Tyr Thr Asn Ile Lys Glu Lys Ala Asn Ala Leu Glu
        115                 120                 125

Phe Asn Val Gln Leu Lys Gly Arg Val Cys Asp Thr Phe Leu Phe Ala
```

```
            130                 135                 140
Gln Asp Tyr Phe Gly Ser Tyr Asp Ile Cys Ile Thr Asn Pro Pro Trp
145                 150                 155                 160

Val Ile Ile Lys Pro Asp Lys Lys Glu Lys Glu Arg Leu Ser Lys Glu
                165                 170                 175

Glu Glu Ile Glu Tyr Ile Glu Ile Leu Lys Asn Phe Asp Asp Phe Leu
                180                 185                 190

Ser Arg Tyr Tyr Pro Thr Ser Leu Pro Thr Lys Lys Tyr Gly Gly Trp
                195                 200                 205

Gly Thr Asn Leu Ala Arg Cys Gly Thr Glu Val Ala Leu Arg Leu Ile
                210                 215                 220

Ser Lys Val Gly Ile Cys Gly Ile Val Ser Pro Ala Ser Leu Leu Gly
225                 230                 235                 240

Asp Gln Val Ser Asp Asn Leu Arg Val Trp Met Phe Asn Asn Tyr Glu
                245                 250                 255

Val Tyr Ser Ile Ser Tyr Phe Val Ala Glu Ala Lys Leu Phe Gly Lys
                260                 265                 270

Val Asp Gln Ala Val Ile Thr Leu Thr Leu Ser Pro Lys Cys Asp Asp
                275                 280                 285

Ser Ser Gly Asp Ile Ile Pro His Leu Phe Tyr Tyr Asp Arg Glu Leu
                290                 295                 300

Phe Glu Lys Arg Tyr Tyr Met Asp Glu Tyr Asp Trp Arg Ile Ile Lys
305                 310                 315                 320

Ser Leu Asn Tyr Val Ile Pro Ile Gln Phe Gly Leu Glu Ile Ile Lys
                325                 330                 335

Met Asn Arg Leu Phe Lys Ser Leu Pro Thr Leu Gly Asp Leu Glu Asn
                340                 345                 350

Glu Lys Glu Gly Ile Trp Leu Gly Arg Glu Leu Asp Glu Thr Gly Ile
                355                 360                 365

Lys Glu Lys Leu Ala Asn Lys Gly Gln Tyr Arg Phe Ile Lys Gly Lys
                370                 375                 380

Met Val Gly Arg Tyr Asn Leu Ile Glu Glu Ser Asn Gln Tyr Ile Asp
385                 390                 395                 400

Val Arg Lys Ile Asp Lys Ile Pro Lys Ser Val Glu Phe Tyr Arg Leu
                405                 410                 415

Val Trp Arg Asp Val Ser Arg Thr Thr Gln Lys Arg Arg Leu Ile Ser
                420                 425                 430

Thr Ile Ile Pro Pro Lys Tyr Ile Thr Gly Asn Ser Leu Asn Val Ala
                435                 440                 445

Tyr Phe Lys Asp Asn Asn Leu Lys Lys Leu Lys Ala Leu Leu Ala Ile
                450                 455                 460

Met Asn Ser Phe Val Phe Glu Ala Gln Val Arg Ala Asn Leu Ser Thr
465                 470                 475                 480

Asn His Ile Ser Leu Gly Ile Ile Arg Arg Ala His Ile Pro Lys Leu
                485                 490                 495

Glu Gly Arg Val Val Asp Glu Leu Ser Gln Leu Val Asp Asn Tyr Val
                500                 505                 510

Asn Glu Glu Ser Glu Leu Leu Leu Glu Val Lys Val Ala Lys Ala Tyr
                515                 520                 525

Gly Leu Ser Phe Glu Asp Phe Ser Ser Ile Leu Ser Leu Phe Asp Lys
                530                 535                 540

Ile Gly Lys Asp Glu Lys Glu Lys Ile Leu Gln Val Ala Lys Lys Tyr
545                 550                 555                 560
```

Leu Lys Gly Gly Ile Lys Asn Asp Ser
                565

<210> SEQ ID NO 3
<211> LENGTH: 1188
<212> TYPE: DNA
<213> ORGANISM: Bacillus stearothermophilus 6-55
<220> FEATURE:
<221> NAME/KEY: CDS
<222> LOCATION: (1)..(1188)
<223> OTHER INFORMATION:

<400> SEQUENCE: 3

| | | |
|---|---|---|
| atg att cct aat cat gtt tca tca aaa tta agt gaa ctt gat atg tta<br>Met Ile Pro Asn His Val Ser Ser Lys Leu Ser Glu Leu Asp Met Leu<br>1               5                   10                  15 | 48 |
| atc att aag cat gta cct cca gga ggt aat tgg aag gac att cca gaa<br>Ile Ile Lys His Val Pro Pro Gly Gly Asn Trp Lys Asp Ile Pro Glu<br>            20                  25                  30 | 96 |
| tgg gtt cct tct aaa aga tta gaa caa ata cga aaa agt tat gca gaa<br>Trp Val Pro Ser Lys Arg Leu Glu Gln Ile Arg Lys Ser Tyr Ala Glu<br>        35                  40                  45 | 144 |
| gga aag gga agt cgt tct acg tat tat ggt aga ctt ctt cca gat atg<br>Gly Lys Gly Ser Arg Ser Thr Tyr Tyr Gly Arg Leu Leu Pro Asp Met<br>    50                  55                  60 | 192 |
| cct tct tat aca ata aac act tat ttt aat aga cca gga aat ggt tgt<br>Pro Ser Tyr Thr Ile Asn Thr Tyr Phe Asn Arg Pro Gly Asn Gly Cys<br>65                  70                  75                  80 | 240 |
| cat ata cat tat gag caa gat agg aca tta tct caa cgt gag gca gct<br>His Ile His Tyr Glu Gln Asp Arg Thr Leu Ser Gln Arg Glu Ala Ala<br>                85                  90                  95 | 288 |
| aga ctt cag tca ttt cct gat gat ttt att ttt tat gga agt aaa aca<br>Arg Leu Gln Ser Phe Pro Asp Asp Phe Ile Phe Tyr Gly Ser Lys Thr<br>            100                 105                 110 | 336 |
| gcc ata aat aat cag att gga aat gca gta ccg ccg tta tta gcg tat<br>Ala Ile Asn Asn Gln Ile Gly Asn Ala Val Pro Pro Leu Leu Ala Tyr<br>        115                 120                 125 | 384 |
| caa ata gct aaa gca ttt ccc ttt aaa gga caa ttt gtc gac ttg ttt<br>Gln Ile Ala Lys Ala Phe Pro Phe Lys Gly Gln Phe Val Asp Leu Phe<br>    130                 135                 140 | 432 |
| agt ggt gca gga ggt ctt tct cta gga ttt tta tgg gca ggt tgg aaa<br>Ser Gly Ala Gly Gly Leu Ser Leu Gly Phe Leu Trp Ala Gly Trp Lys<br>145                 150                 155                 160 | 480 |
| cct ata att gca aat gat att gat aaa tgg gca cta aca act tac atg<br>Pro Ile Ile Ala Asn Asp Ile Asp Lys Trp Ala Leu Thr Thr Tyr Met<br>                165                 170                 175 | 528 |
| aat aac ata cat aat gaa gtt gtt tta ggg gat ata aga gat gaa aaa<br>Asn Asn Ile His Asn Glu Val Val Leu Gly Asp Ile Arg Asp Glu Lys<br>            180                 185                 190 | 576 |
| gta tca gaa aca atc att caa aaa tgc cta ata gca aag aaa agc aat<br>Val Ser Glu Thr Ile Ile Gln Lys Cys Leu Ile Ala Lys Lys Ser Asn<br>        195                 200                 205 | 624 |
| cca gat aga cca ttg ttt gtt tta ggt gga cca cct tgt caa ggt ttt<br>Pro Asp Arg Pro Leu Phe Val Leu Gly Gly Pro Pro Cys Gln Gly Phe<br>    210                 215                 220 | 672 |
| tct act gct gga aaa aag cgt agc ata gta gat gaa aga aac tgg ctt<br>Ser Thr Ala Gly Lys Lys Arg Ser Ile Val Asp Glu Arg Asn Trp Leu<br>225                 230                 235                 240 | 720 |
| ttt gaa tct tac gta tca ata tta aaa gaa gtt aaa cca gat gga ttt<br>Phe Glu Ser Tyr Val Ser Ile Leu Lys Glu Val Lys Pro Asp Gly Phe<br>                245                 250                 255 | 768 |

```
att ttt gaa aat gta aca ggt tta tta agt atg gaa aaa ggt gcg ttt         816
Ile Phe Glu Asn Val Thr Gly Leu Leu Ser Met Glu Lys Gly Ala Phe
        260                 265                 270 ttt gaa atg gtt aag tca gaa tta agt aaa aca gtt tct aac cta ttt         864
Phe Glu Met Val Lys Ser Glu Leu Ser Lys Thr Val Ser Asn Leu Phe
    275                 280                 285 gta tat aaa cta aat agt gta gat tat ggg gtt cct cag aga aga aat         912
Val Tyr Lys Leu Asn Ser Val Asp Tyr Gly Val Pro Gln Arg Arg Asn
290                 295                 300 agg gta gta atc ata ggt gac tca acg ggt act aaa aac agt gaa cca         960
Arg Val Val Ile Ile Gly Asp Ser Thr Gly Thr Lys Asn Ser Glu Pro
305                 310                 315                 320 cca att cct att aca tct cta aaa ggt gag aaa aca tta ttt gat gcc        1008
Pro Ile Pro Ile Thr Ser Leu Lys Gly Glu Lys Thr Leu Phe Asp Ala
            325                 330                 335 ctt tca tca gcc ata tca gta aaa gaa gct tta tct gat tta cca ttg        1056
Leu Ser Ser Ala Ile Ser Val Lys Glu Ala Leu Ser Asp Leu Pro Leu
        340                 345                 350 ctt tct cct aat gaa gat ggc tct tgg aaa aat tat gtt tgt gag cca        1104
Leu Ser Pro Asn Glu Asp Gly Ser Trp Lys Asn Tyr Val Cys Glu Pro
    355                 360                 365 cag aat atc tat caa agt ttt atg agg aaa aag att act gct caa caa        1152
Gln Asn Ile Tyr Gln Ser Phe Met Arg Lys Lys Ile Thr Ala Gln Gln
370                 375                 380 tat ata gaa atg ttg agc agt tta gcg ata ata taa                        1188
Tyr Ile Glu Met Leu Ser Ser Leu Ala Ile Ile
385                 390                 395
```

<210> SEQ ID NO 4
<211> LENGTH: 395
<212> TYPE: PRT
<213> ORGANISM: Bacillus stearothermophilus 6-55

<400> SEQUENCE: 4

```
Met Ile Pro Asn His Val Ser Ser Lys Leu Ser Glu Leu Asp Met Leu
1               5                   10                  15

Ile Ile Lys His Val Pro Pro Gly Gly Asn Trp Lys Asp Ile Pro Glu
            20                  25                  30

Trp Val Pro Ser Lys Arg Leu Glu Gln Ile Arg Lys Ser Tyr Ala Glu
        35                  40                  45

Gly Lys Gly Ser Arg Ser Thr Tyr Tyr Gly Arg Leu Leu Pro Asp Met
    50                  55                  60

Pro Ser Tyr Thr Ile Asn Thr Tyr Phe Asn Arg Pro Gly Asn Gly Cys
65                  70                  75                  80

His Ile His Tyr Glu Gln Asp Arg Thr Leu Ser Gln Arg Glu Ala Ala
                85                  90                  95

Arg Leu Gln Ser Phe Pro Asp Asp Phe Ile Phe Tyr Gly Ser Lys Thr
            100                 105                 110

Ala Ile Asn Asn Gln Ile Gly Asn Ala Val Pro Pro Leu Leu Ala Tyr
        115                 120                 125

Gln Ile Ala Lys Ala Phe Pro Phe Lys Gly Gln Phe Val Asp Leu Phe
    130                 135                 140

Ser Gly Ala Gly Gly Leu Ser Leu Gly Phe Leu Trp Ala Gly Trp Lys
145                 150                 155                 160

Pro Ile Ile Ala Asn Asp Ile Asp Lys Trp Ala Leu Thr Thr Tyr Met
                165                 170                 175

Asn Asn Ile His Asn Glu Val Val Leu Gly Asp Ile Arg Asp Glu Lys
```

-continued

```
                    180                 185                 190
Val Ser Glu Thr Ile Ile Gln Lys Cys Leu Ile Ala Lys Lys Ser Asn
            195                 200                 205

Pro Asp Arg Pro Leu Phe Val Leu Gly Gly Pro Pro Cys Gln Gly Phe
    210                 215                 220

Ser Thr Ala Gly Lys Lys Arg Ser Ile Val Asp Glu Arg Asn Trp Leu
225                 230                 235                 240

Phe Glu Ser Tyr Val Ser Ile Leu Lys Glu Val Lys Pro Asp Gly Phe
                245                 250                 255

Ile Phe Glu Asn Val Thr Gly Leu Leu Ser Met Glu Lys Gly Ala Phe
            260                 265                 270

Phe Glu Met Val Lys Ser Glu Leu Ser Lys Thr Val Ser Asn Leu Phe
            275                 280                 285

Val Tyr Lys Leu Asn Ser Val Asp Tyr Gly Val Pro Gln Arg Arg Asn
    290                 295                 300

Arg Val Val Ile Ile Gly Asp Ser Thr Gly Thr Lys Asn Ser Glu Pro
305                 310                 315                 320

Pro Ile Pro Ile Thr Ser Leu Lys Gly Glu Lys Thr Leu Phe Asp Ala
                325                 330                 335

Leu Ser Ser Ala Ile Ser Val Lys Glu Ala Leu Ser Asp Leu Pro Leu
            340                 345                 350

Leu Ser Pro Asn Glu Asp Gly Ser Trp Lys Asn Tyr Val Cys Glu Pro
            355                 360                 365

Gln Asn Ile Tyr Gln Ser Phe Met Arg Lys Lys Ile Thr Ala Gln Gln
    370                 375                 380

Tyr Ile Glu Met Leu Ser Ser Leu Ala Ile Ile
385                 390                 395

<210> SEQ ID NO 5
<211> LENGTH: 1635
<212> TYPE: DNA
<213> ORGANISM: Bacillus stearothermophilus 6-55
<220> FEATURE:
<221> NAME/KEY: CDS
<222> LOCATION: (1)..(1635)
<223> OTHER INFORMATION:

<400> SEQUENCE: 5 ttg gga aaa aaa gct gaa tat gga cag gga cat cca ata ttt tta gaa      48
Leu Gly Lys Lys Ala Glu Tyr Gly Gln Gly His Pro Ile Phe Leu Glu
1               5                   10                  15 tat gct gaa cag ata atc caa cat aaa gaa tac caa ggt atg cca gac      96
Tyr Ala Glu Gln Ile Ile Gln His Lys Glu Tyr Gln Gly Met Pro Asp
            20                  25                  30 tta aga tac cct gat gga aga att cag tgg gaa gca cct tca aat aga     144
Leu Arg Tyr Pro Asp Gly Arg Ile Gln Trp Glu Ala Pro Ser Asn Arg
        35                  40                  45 aaa agc ggt ata ttt aaa gac act aac att aag cga aga aaa tgg tgg     192
Lys Ser Gly Ile Phe Lys Asp Thr Asn Ile Lys Arg Arg Lys Trp Trp
    50                  55                  60 gaa caa aaa gct att tct atc ggg ata gac cct tct agt aat caa tgg     240
Glu Gln Lys Ala Ile Ser Ile Gly Ile Asp Pro Ser Ser Asn Gln Trp
65                  70                  75                  80 att agt aag aca gcc aaa tta att cat cca aca atg aga aaa cct tgc     288
Ile Ser Lys Thr Ala Lys Leu Ile His Pro Thr Met Arg Lys Pro Cys
                85                  90                  95 aaa aag tgc gga agg ata atg gat tta cga tat agc tat cct acc aaa     336
Lys Lys Cys Gly Arg Ile Met Asp Leu Arg Tyr Ser Tyr Pro Thr Lys
```

```
                100                 105                 110
aat ctt att aaa cgc att aga aaa tta cct tat gtt gat gaa tcg ttt         384
Asn Leu Ile Lys Arg Ile Arg Lys Leu Pro Tyr Val Asp Glu Ser Phe
            115                 120                 125 gaa att gat tca cta gaa cat att tta aaa ctt att aaa cgt tta gtt         432
Glu Ile Asp Ser Leu Glu His Ile Leu Lys Leu Ile Lys Arg Leu Val
        130                 135                 140 cta caa tat ggt gat aaa gta tac gat gat ttg cct aaa cta cta act         480
Leu Gln Tyr Gly Asp Lys Val Tyr Asp Asp Leu Pro Lys Leu Leu Thr
145                 150                 155                 160 tgc aaa gca gtt aaa aat att cca aga ttg gga aac gat tta gat act         528
Cys Lys Ala Val Lys Asn Ile Pro Arg Leu Gly Asn Asp Leu Asp Thr
                165                 170                 175 tgg tta aat tgg att gat tct gtt tat att ccg agt gaa cct agt atg         576
Trp Leu Asn Trp Ile Asp Ser Val Tyr Ile Pro Ser Glu Pro Ser Met
            180                 185                 190 ctt agt cca ggc gct atg gca aat ccg cca gat aga tta gat ggg ttc         624
Leu Ser Pro Gly Ala Met Ala Asn Pro Pro Asp Arg Leu Asp Gly Phe
        195                 200                 205 cac tca tta aat gaa tgc tgt aga agt cat gct gat aga ggt aga tgg         672
His Ser Leu Asn Glu Cys Cys Arg Ser His Ala Asp Arg Gly Arg Trp
    210                 215                 220 gaa aaa aac ctg cgg tca tat aca aca gat aga aga gca ttt gaa tac         720
Glu Lys Asn Leu Arg Ser Tyr Thr Thr Asp Arg Arg Ala Phe Glu Tyr
225                 230                 235                 240 tgg gtt gat gga gat tgg gtt gca gct gac aaa ctt atg gga cta ata         768
Trp Val Asp Gly Asp Trp Val Ala Ala Asp Lys Leu Met Gly Leu Ile
                245                 250                 255 aga aca aat gaa cag ata aag aag gaa act tgt tta aat gat aac cac         816
Arg Thr Asn Glu Gln Ile Lys Lys Glu Thr Cys Leu Asn Asp Asn His
            260                 265                 270 cca ggc cct tgt tct gca gac cat att ggt cct att tcc ctt ggt ttt         864
Pro Gly Pro Cys Ser Ala Asp His Ile Gly Pro Ile Ser Leu Gly Phe
        275                 280                 285 gtt cac agg cca gag ttt caa ttg cta tgt aac tca tgt aac agt gcc         912
Val His Arg Pro Glu Phe Gln Leu Leu Cys Asn Ser Cys Asn Ser Ala
    290                 295                 300 aaa aat aat cga atg act ttt tca gat gtc caa cac tta att aat gcg         960
Lys Asn Asn Arg Met Thr Phe Ser Asp Val Gln His Leu Ile Asn Ala
305                 310                 315                 320 gaa aat aat gga gaa gag gtt gca tct tgg tac tgt aaa cat ata tgg        1008
Glu Asn Asn Gly Glu Glu Val Ala Ser Trp Tyr Cys Lys His Ile Trp
                325                 330                 335 gat tta aga aaa cat gat gtt aaa aac aac gaa aac gca ttg aga tta        1056
Asp Leu Arg Lys His Asp Val Lys Asn Asn Glu Asn Ala Leu Arg Leu
            340                 345                 350 agt aaa att tta aga gat aat cgc cat aca gct atg ttt ata tta agt        1104
Ser Lys Ile Leu Arg Asp Asn Arg His Thr Ala Met Phe Ile Leu Ser
        355                 360                 365 gag tta tta aaa gat aat cac tat ctt ttc ctt tca act ttt tta gga        1152
Glu Leu Leu Lys Asp Asn His Tyr Leu Phe Leu Ser Thr Phe Leu Gly
    370                 375                 380 tta cag tat gca gaa agg tct gta agt ttt tca aat ata aaa att gaa        1200
Leu Gln Tyr Ala Glu Arg Ser Val Ser Phe Ser Asn Ile Lys Ile Glu
385                 390                 395                 400 aat cat att atc aca gga caa att tct gaa caa cca aga gat aca aaa        1248
Asn His Ile Ile Thr Gly Gln Ile Ser Glu Gln Pro Arg Asp Thr Lys
                405                 410                 415
```

```
tac act gaa gag caa aaa gcc aga aga atg aga att gga ttc gaa gca      1296
Tyr Thr Glu Glu Gln Lys Ala Arg Arg Met Arg Ile Gly Phe Glu Ala
            420                 425                 430 ctt aaa agc tat att gaa aaa gaa aac aga aat gcc tta tta gta ata      1344
Leu Lys Ser Tyr Ile Glu Lys Glu Asn Arg Asn Ala Leu Leu Val Ile
        435                 440                 445 aat gat aaa att att gat aaa att aac gaa ata aaa aat ata tta caa      1392
Asn Asp Lys Ile Ile Asp Lys Ile Asn Glu Ile Lys Asn Ile Leu Gln
450                 455                 460 gat att cca gac gaa tat aaa ctt tta aat gaa aaa atc tct gag caa      1440
Asp Ile Pro Asp Glu Tyr Lys Leu Leu Asn Glu Lys Ile Ser Glu Gln
465                 470                 475                 480 ttc aac agt gaa gaa gtt tct gat gaa cta ctc aga gat tta gtt act      1488
Phe Asn Ser Glu Glu Val Ser Asp Glu Leu Leu Arg Asp Leu Val Thr
                485                 490                 495 cat ctc cca act aaa gaa agt gaa cca gct aac ttt aaa ttg gct aga      1536
His Leu Pro Thr Lys Glu Ser Glu Pro Ala Asn Phe Lys Leu Ala Arg
            500                 505                 510 aaa tac ttg caa gaa ata atg gaa ata gta gga gat gaa ctt tca aaa      1584
Lys Tyr Leu Gln Glu Ile Met Glu Ile Val Gly Asp Glu Leu Ser Lys
        515                 520                 525 atg tgg gaa gat gaa cga tac gta aga caa aca ttt gca gat tta gat      1632
Met Trp Glu Asp Glu Arg Tyr Val Arg Gln Thr Phe Ala Asp Leu Asp
530                 535                 540 taa                                                                   1635

<210> SEQ ID NO 6
<211> LENGTH: 544
<212> TYPE: PRT
<213> ORGANISM: Bacillus stearothermophilus 6-55

<400> SEQUENCE: 6

Leu Gly Lys Lys Ala Glu Tyr Gly Gln Gly His Pro Ile Phe Leu Glu
1               5                   10                  15

Tyr Ala Glu Gln Ile Ile Gln His Lys Glu Tyr Gln Gly Met Pro Asp
            20                  25                  30

Leu Arg Tyr Pro Asp Gly Arg Ile Gln Trp Glu Ala Pro Ser Asn Arg
        35                  40                  45

Lys Ser Gly Ile Phe Lys Asp Thr Asn Ile Lys Arg Arg Lys Trp Trp
    50                  55                  60

Glu Gln Lys Ala Ile Ser Ile Gly Ile Asp Pro Ser Ser Asn Gln Trp
65                  70                  75                  80

Ile Ser Lys Thr Ala Lys Leu Ile His Pro Thr Met Arg Lys Pro Cys
                85                  90                  95

Lys Lys Cys Gly Arg Ile Met Asp Leu Arg Tyr Ser Tyr Pro Thr Lys
            100                 105                 110

Asn Leu Ile Lys Arg Ile Arg Lys Leu Pro Tyr Val Asp Glu Ser Phe
        115                 120                 125

Glu Ile Asp Ser Leu Glu His Ile Leu Lys Leu Ile Lys Arg Leu Val
    130                 135                 140

Leu Gln Tyr Gly Asp Lys Val Tyr Asp Leu Pro Lys Leu Leu Thr
145                 150                 155                 160

Cys Lys Ala Val Lys Asn Ile Pro Arg Leu Gly Asn Asp Leu Asp Thr
                165                 170                 175

Trp Leu Asn Trp Ile Asp Ser Val Tyr Ile Pro Ser Glu Pro Ser Met
            180                 185                 190
```

```
Leu Ser Pro Gly Ala Met Ala Asn Pro Pro Asp Arg Leu Asp Gly Phe
            195                 200                 205

His Ser Leu Asn Glu Cys Cys Arg Ser His Ala Asp Arg Gly Arg Trp
            210                 215                 220

Glu Lys Asn Leu Arg Ser Tyr Thr Thr Asp Arg Arg Ala Phe Glu Tyr
225                 230                 235                 240

Trp Val Asp Gly Asp Trp Val Ala Ala Asp Lys Leu Met Gly Leu Ile
                245                 250                 255

Arg Thr Asn Glu Gln Ile Lys Lys Glu Thr Cys Leu Asn Asp Asn His
            260                 265                 270

Pro Gly Pro Cys Ser Ala Asp His Ile Gly Pro Ile Ser Leu Gly Phe
            275                 280                 285

Val His Arg Pro Glu Phe Gln Leu Leu Cys Asn Ser Cys Asn Ser Ala
    290                 295                 300

Lys Asn Asn Arg Met Thr Phe Ser Asp Val Gln His Leu Ile Asn Ala
305                 310                 315                 320

Glu Asn Asn Gly Glu Glu Val Ala Ser Trp Tyr Cys Lys His Ile Trp
                325                 330                 335

Asp Leu Arg Lys His Asp Val Lys Asn Asn Glu Asn Ala Leu Arg Leu
            340                 345                 350

Ser Lys Ile Leu Arg Asp Asn Arg His Thr Ala Met Phe Ile Leu Ser
            355                 360                 365

Glu Leu Leu Lys Asp Asn His Tyr Leu Phe Leu Ser Thr Phe Leu Gly
    370                 375                 380

Leu Gln Tyr Ala Glu Arg Ser Val Ser Phe Ser Asn Ile Lys Ile Glu
385                 390                 395                 400

Asn His Ile Ile Thr Gly Gln Ile Ser Glu Gln Pro Arg Asp Thr Lys
                405                 410                 415

Tyr Thr Glu Glu Gln Lys Ala Arg Arg Met Arg Ile Gly Phe Glu Ala
            420                 425                 430

Leu Lys Ser Tyr Ile Glu Lys Glu Asn Arg Asn Ala Leu Leu Val Ile
            435                 440                 445

Asn Asp Lys Ile Ile Asp Lys Ile Asn Glu Ile Lys Asn Ile Leu Gln
    450                 455                 460

Asp Ile Pro Asp Glu Tyr Lys Leu Leu Asn Glu Lys Ile Ser Glu Gln
465                 470                 475                 480

Phe Asn Ser Glu Glu Val Ser Asp Glu Leu Leu Arg Asp Leu Val Thr
                485                 490                 495

His Leu Pro Thr Lys Glu Ser Glu Pro Ala Asn Phe Lys Leu Ala Arg
            500                 505                 510

Lys Tyr Leu Gln Glu Ile Met Glu Ile Val Gly Asp Glu Leu Ser Lys
            515                 520                 525

Met Trp Glu Asp Glu Arg Tyr Val Arg Gln Thr Phe Ala Asp Leu Asp
    530                 535                 540

<210> SEQ ID NO 7
<211> LENGTH: 27
<212> TYPE: DNA
<213> ORGANISM: inverse PCR primers

<400> SEQUENCE: 7
agataaatta gctcttactt gagcttc                                27

<210> SEQ ID NO 8
<211> LENGTH: 24
```

```
<212> TYPE: DNA
<213> ORGANISM: inverse PCR primers

<400> SEQUENCE: 8
ggagagcaca tataccgaag ttag                                    24

<210> SEQ ID NO 9
<211> LENGTH: 24
<212> TYPE: DNA
<213> ORGANISM: inverse PCR primers

<400> SEQUENCE: 9
gctcttcagt gtattttgta tctc                                    24

<210> SEQ ID NO 10
<211> LENGTH: 24
<212> TYPE: DNA
<213> ORGANISM: inverse PCR primers

<400> SEQUENCE: 10
tgagaattgg attcgaagca ctta                                    24

<210> SEQ ID NO 11
<211> LENGTH: 24
<212> TYPE: DNA
<213> ORGANISM: inverse PCR primers

<400> SEQUENCE: 11
gagatagagt atattgaaat acta                                    24

<210> SEQ ID NO 12
<211> LENGTH: 24
<212> TYPE: DNA
<213> ORGANISM: inverse PCR primers

<400> SEQUENCE: 12
ttacccatgg cgggtttgta atac                                    24

<210> SEQ ID NO 13
<211> LENGTH: 24
<212> TYPE: DNA
<213> ORGANISM: inverse PCR primers

<400> SEQUENCE: 13
tctgcagaac aagggcctgg gtgg                                    24

<210> SEQ ID NO 14
<211> LENGTH: 25
<212> TYPE: DNA
<213> ORGANISM: inverse PCR primers

<400> SEQUENCE: 14
catattggtc ctattttccc ttggt                                   25

<210> SEQ ID NO 15
<211> LENGTH: 24
<212> TYPE: DNA
<213> ORGANISM: inverse PCR primers

<400> SEQUENCE: 15
caatttaacc aagtatctaa atcg                                    24
```

<210> SEQ ID NO 16
<211> LENGTH: 24
<212> TYPE: DNA
<213> ORGANISM: inverse PCR primers

<400> SEQUENCE: 16
ttctgtttat attccgagtg aacc                                    24

<210> SEQ ID NO 17
<211> LENGTH: 54
<212> TYPE: DNA
<213> ORGANISM: PCR primers

<400> SEQUENCE: 17
ggtggtgcta gcggaggtaa ataaatgaaa gaaaacacag aaattaatat agat    54

<210> SEQ ID NO 18
<211> LENGTH: 39
<212> TYPE: DNA
<213> ORGANISM: PCR primers

<400> SEQUENCE: 18
ggtggtgcat gcctaatata tttcttggta cgtcattt                     39

<210> SEQ ID NO 19
<211> LENGTH: 33
<212> TYPE: DNA
<213> ORGANISM: PCR primers

<400> SEQUENCE: 19
ggtggtcata tgggaaaaaa agctgaatat gga                          33

<210> SEQ ID NO 20
<211> LENGTH: 36
<212> TYPE: DNA
<213> ORGANISM: PCR primers

<400> SEQUENCE: 20
ggtggtggat cctcattaat ctaaatctgc aaatgt                       36

<210> SEQ ID NO 21
<211> LENGTH: 48
<212> TYPE: DNA
<213> ORGANISM: PCR primers

<400> SEQUENCE: 21
ggtggtggat ccggaggtaa ataaatgagt aatgctaaaa gtttctct          48

<210> SEQ ID NO 22
<211> LENGTH: 36
<212> TYPE: DNA
<213> ORGANISM: PCR primers

<400> SEQUENCE: 22
ggtggtgcat gcttatatta tcgctaaact gctcaa                       36

<210> SEQ ID NO 23
<211> LENGTH: 20
<212> TYPE: PRT
<213> ORGANISM: Bacillus stearothermophilus 6-55

-continued

```
<400> SEQUENCE: 23

Met Gly Lys Lys Ala Glu Tyr Gly Gln Gly His Pro Ile Phe Leu Glu
1               5                   10                  15

Tyr Ala Glu Gln
            20
```

US 6,723,546 B2

METHOD FOR CLONING AND EXPRESSION OF BSAI RESTRICTION ENDONUCLEASE AND BSAI METHYLASE IN *E. COLI*

BACKGROUND OF THE INVENTION

The present invention relates to recombinant DNA encoding the BsaI restriction endonuclease (BsaI endonuclease or BsaI) as well as BsaI methyltransferases (BsaI methylases, M. BsaIA and M.BsaIB, or M. BsaIAB), as well as expression of BsaI endonuclease and methylase in *E. coli* cells containing the recombinant DNA.

BsaI endonuclease is found in the strain of *Bacillus stearothermophilus* 6–55 (New England Biolabs' strain collection #481; Beverly, Mass.) It binds to the double-stranded DNA sequence 5'GGTCTC3' N1/N5 and cleaves downstream sequence at N1 (top strand) and N5 (bottom strand) to generate a 4-base 5' overhang (/ indicates the cleavage of phosphodiester bond). BsaI methylases (M.BsaIA and M.BsaIB) are also found in the same strain. M.BsaIA is an adenine methylase, presumably modifying the adenine on the bottom strand (5'GAGACC3'). M.BsaIB is a C5 methylase and presumably modifies the top strand of BsaI site.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') on DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313 (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178:717–719 (1980); HhaII: Mann et al., Gene 3:97–112 (1978); PstI: Walder et al., Proc. Nat. Acad. Sci. 78:1503–1507 (1981)). Since the expressions of restriction-modification systems in bacteria enable them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12:3659–3676 (1984); PaeR7: Gingeras and Brooks, Proc. Natl. Acad. Sci. USA 80:402–406 (1983); Theriault and Roy, Gene 19:355–359 (1982); PvuII: Blumenthal et al., J. Bacteriol. 164:501–509 (1985); Tsp45I: Wayne et al. Gene 202:83–88 (1997)).

A third approach is to select for active expression of methylase genes (methylase selection) (U.S. Pat. No. 5,200, 333 and BsuRI: Kiss et al., Nucl. Acids. Res. 13:6403–6421 (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225 (1980); BcnI: Janulaitis et al., Gene 20:197–204 (1982); BsuRI: Kiss and Baldauf, Gene 21:111–119 (1983); and MspI: Walder et al., J. Biol. Chem. 258:1235–1241, (1983)).

A more recent method, the "endo-blue method", has been described for direct cloning of thermostable restriction endonuclease genes into *E. coli* based on the indicator strain of *E. coli* containing the dinD::lacZ fusion (U.S. Pat. No. 5,498,535; Fomenkov et al., Nucl. Acids Res. 22:2399–2403 (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of DNA methylases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632 (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) can also make the DNA resistant to PspGI restriction digestion. Another example is that CpG methylase can modify the CG dinucloetide and make the NotI site (5'GCGGCCGC3') refractory to NotI digestion (New England Biolabs' Catalog, 2000–01, page 220; Beverly, Mass.). Therefore methylases can be used as a tool to modify certain DNA sequences and make them uncleavable by restriction enzymes.

Type II methylase genes have been found in many sequenced bacterial genomes (GenBank, http://www.ncbi.nlm.nih.gov; and Rebase, http://rebase.neb.com/rebase). Direct cloning and over-expression of ORFs adjacent to the methylase genes yielded restriction enzymes with novel specificities (Kong et al. Nucl. Acids Res. 28:3216–3223 (2000)). Thus microbial genome mining emerged as a new way of screening/cloning new type II restriction enzymes and methylases and their isoschizomers.

Because purified restriction endonucleases and modification methylases are useful tools for creating recombinant molecules in the laboratory, there is a great commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning BsaI endonuclease gene (bsaIR) from *Bacillus stearothermophilus* 6–55 into *E. coli* by inverse PCR and direct PCR amplification from genomic DNA. The inverse PCR primer sequences are based on the BsaI methylase gene (bsaIMB) sequence that derived from methylase selection.

It proved difficult to clone the bsaIM genes by the standard methylase selection method. ApoI, Sau3AI, and NlaIII partial genomic DNA libraries were constructed using a modified cloning vector pRRS (Ap$_R$). No methylase positive clones were identified following BsaI challenge and methylase selection. To increase the selection efficiency, a second step of mung bean nuclease treatment was included following BsaI digestion, which destroyed the DNA ends and inactivated the β-lactamase gene. This additional step increased the methylase selection efficiency and generated 20 BsaI resistant clones.

Since restriction gene is usually located in close proximity to the cognate methylase gene in a particular R-M system, inverse PCR was employed to clone the adjacent DNA surrounding the bsaIMB gene. Open reading frames (ORF) were identified on both sides of the bsaIMB gene. A second methylase gene was found upstream and the restriction gene was found downstream.

BsmAI site (5'GTCTC) overlaps with BsaI site (5'GGTCTC) and M.BsmAI protects *E. coli* chromosome DNA against BsaI digestion. To express bsaIR gene in *E. coli*, a non-cognate methylase gene, bsmAIM gene (M1::M2 fusion) was first cloned in pBR322 to pre-modify T7 expression host ER2566. The bsaIR gene was amplified by PCR, ligated to pACYC-T7ter with compatible ends, and transformed into pre-modified host ER2566 [pBR322-BsmAIM].

Transformants were cultured and BsaI endonuclease activity was detected in IPTG-induced cell extracts. Three clones with high BsaI activity were sequenced and clone #5 was confirmed to contain the wild type sequence.

Two more expression strains were constructed using the cognate methylase genes, ER2566 [pBR-BsaIMA&B, pACYC-T7ter-BsaIR] or ER2683 [pACYC-BsaIMA&B, pUC19-BsaIR]. Neither strain generated more BsaI units per gram of wet cells. Therefore, the non-cognate methylase modified strain ER2556 [pBR322-BsmAIM1M2, pACYC-T7ter-BsaI] was used as the BsaI production strain.

BRIEF DESCRIPTION OF THE DRAWINGS

FIG. 2 DNA sequence of M.BsaIA gene (bsaIMA, 1710 bp) (SEQ ID NO:1) and its encoded amino acid sequence (SEQ ID NO:2).

FIG. 3 DNA sequence of M.BsaB gene (bsaIMB, 1188 bp) (SEQ ID NO:3) and its encoded amino acid sequence (SEQ ID NO:4).

FIG. 4 DNA sequence of BsaI endonuclease gene (bsaIR, 1635 bp) (SEQ ID NO:5) and its encoded amino acid sequence (SEQ ID NO:6).

DETAILED DESCRIPTION OF THE INVENTION

Figure 1:
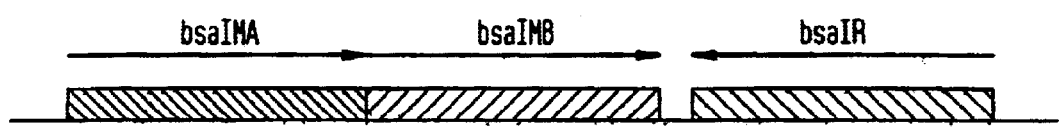
FIG. 1 Gene organization of BsaI restriction-modification system. bsaIMA, BsaI methylase 1 gene; bsaIMB. BsaI methylase 2 gene; bsaIR, bsaI restriction endonuclease gene.
Figure 5:
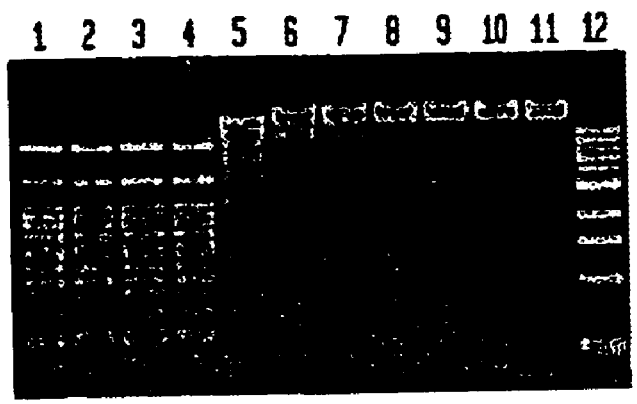
FIG. 5 Recombinant BsaI restriction endonuclease activity assay using cell extract. Lane 1, positive control, T7 DNA digested with purified native BsaI, lanes 2 to 11, T7 DNA treated with diluted cell extract containing recombinant BsaI endonuclease; The dilution factors in lanes 2 to 11 were: 1:100, 1:200, 1:400, 1:800, 1:1600, 1:3200, 1:6400, 1:12800, 1:25600, 1:51200. Lane 12, 1 kb DNA size marker.

It was difficult to isolate M.BsaI positive clones among the ApoI, Sau3AI, and NlaIII genomic DNA libraries. After BsaI challenge of ApoI, Sau3AI, and NlaIII plasmid DNA libraries, the digested DNA was transferred into ER2502 to screen M.BsaI positive clones. However, after screening 36 Ap$^R$ survivors, no M.BsaI positive clones were identified. In order to increase the BsaI challenge efficiency and reduce the background of transformation, the BsaI-digested DNA was further treated with mung bean nuclease. This nuclease removes the 4-base ends and causes open reading frame shift in the β-lactamase gene, thus inactivating the Ap$^R$ gene. This strategy proved successful in cloning the bsaIMB gene.

The method described herein by which the bsaIMA, bsaIMB, and bsaIR genes are preferably cloned and expressed in *E. coli* using the following steps:

1. Construction of Genomic DNA Libraries and Methylase Selection

Genomic DNA was prepared from *Bacillus stearothermophilus* 6–55 and digested with restriction enzymes ApoI, Sau3AI, and NlaIII. Genomic DNA libraries were constructed using a modified pRRS vector with two BsaI sites. The ligated DNA was transferred into restriction minus *E. coli* ER2502 competent cell by transformation. Approximately 10$^4$ transformants were pooled and amplified overnight in 0.5 L culture. Primary plasmid DNA libraries were prepared by Qiagen Maxi column method and challenged with BsaI and mung bean nuclease. Following digestion, the plasmids were transformed into ER2502. Plasmids were prepared from Ap$^R$ survivors and screened for resistance to BsaI digestion. The resistant clones were identified as true methylase positive clones by DNA sequencing. The entire insert was sequenced with pUC19 primers and custom-made primers. One ORF of 1188 bp was found and was named bsaIMB, encoding a 395-aa protein with predicted molecular mass of 44.4 kDa. M.BsaIB shows extensive homology with other C5 methylases. However, the conserved motifs IX and X are located at the N-terminus instead of at C-terminus. Inverse PCR was used to amplify the adjacent DNA sequence. After five rounds of inverse PCR two more genes were identified. The upstream gene, bsaIMA, is 1710 bp, encoding an amino-methyltransferase (569-aa protein) with predicted molecular mass of 65.7 kDa.

2. Cloning of bsaIR Gene by Inverse PCR

Inverse PCR primers were made based on the DNA sequence of bsaIMB gene. Genomic DNA was digested with restriction enzymes with 4–6 base recognition sequences and self-ligated. The circular DNA molecules were used as the templates for inverse PCR. Inverse PCR products downstream of bsaIMB were obtained, gel-purified and sequenced. An ORF of 1635 bp was found downstream of the bsaIMB gene. This ORF was named bsaIR gene. It encodes a 544-aa protein with predicted molecular mass of 63.7 kDa.

3. Cloning of bsmAIM Gene into pBR322 to Construct a Premodified Host

Since BsmAI recognition sequence (5'GTCTC') overlaps with BsaI recognition sequence (5'GGTCTC3'), M.BsmAI cross-protects *E. coli* chromosome DNA and plasmid DNA against BsaI digestion. Efforts were made to over-express M.BsmAI first and to construct a pre-modified expression host (BsmAI restriction-modification filed Sep. 20, 2001 received U.S. Ser. No. 09/957,005).

The bsmAIM gene was amplified from the genomic DNA by PCR using two primers. The PCR DNA was digested with NheI and SphI and ligated to pBR322 with compatible ends. The pre-modified host ER2566 [pBR322-BsmAIM] was used for over-expression of bsaIR gene in *E. coli*.

4. Expression of bsaIR Gene in T7 Expression Vector pACYC-T7ter

A BamHI fragment containing bsaIR gene was cloned into pACYC-T7ter expression vector. The ligated DNA was transformed into pre-modified host ER2566 [pBR322-BsmAIM]. Ap$^R$ Cm$^R$ transformants were cultured and induced with IPTG. Recombinant BsaI activity was detected in the supernatant of IPTG-induced cell extracts. Plasmids were extracted from those clones with high BsaI activity. After sequencing the insert, the clone with wild type sequence was used for stability study and purification of BsaI endonuclease.

5. Expression of bsaIR Gene in Cognate Methylase-Modified Host.

A second expression strain was constructed using the cognate methylase genes, ER2566 [pBR-BsaIMA&B, pACYC-T7ter-BsaIR]. The recombinant BsaI yield from this expression clone was estimated at 0.7–1.4×10$^6$ units BsaI/g of wet cell. The first expression strain ER2566 [pBR322-BsmAIM1M2, pACYC-T7ter-BsaIR] produces 1.0–2.0×10$^6$ units of BsaI/g of wet cell. A third expression strain was also constructed in which the bsaIMA and bsaIMB genes were expressed from pACYC184 and the bsaIR gene was expressed from pUC19, ER2683 [pACYC-BsaIMA&B, pUC19-BsaIR]. This strain also generated less BsaI units per gram of wet cells. Therefore, the strain ER2556 [pBR322-BsmAIM1M2, pACYC-T7ter-BsaI] described in section 4 was used as the BsaI production strain.

6. Purification of BsaI Restriction Endonuclease

IPTG-induced cell extracts containing recombinant BsaI endonuclease was purified by heat treatment at 55° C. for one hour to denature *E. coli* proteins. The heat-denatured proteins were removed by centrifugation. The supernatant with BsaI activity was further purified by chromatography through Heparin-Sepharose and DEAE-Sepharose columns. The purified BsaI protein was analyzed on SDS-PAGE and the N-terminus of the recombinant BsaI protein was sequenced to obtain the first 20 aa residues. The actual aa sequence was in total agreement with the predicted aa sequence based on the DNA coding sequence.

The present invention is further illustrated by the following Example. This Example is provided to aid in the understanding of the invention and is not construed as a limitation thereof.

The references cited above and below are herein incorporated by reference.

EXAMPLE I

Cloning of BsaI Restriction-Modification System in *E. coli*

1. Preparation of Genomic DNA and Restriction Digestion of Genomic DNA and Construction of Genomic DNA Libraries Genomic DNA was prepared from *Bacillus stearothermophilus* 6–55 (New England Biolabs' collection #481; Beverly, Mass.) by the standard procedure consisting of the following steps:

(a) cell lysis by addition of lysozyme (2 mg/ml final), sucrose (1% final), and 50 mM Tris-HCl, pH 8.0;

(b) cell lysis by addition of 10% SDS (final concentration 0. 1%);

(c) further cell lysis by addition of 1% Triton X-100 and 62 mM EDTA, 50 mM Tris-HCl, pH 8.0;

(d) Phenol-CHCl$_3$ extraction of DNA 3 times (equal volume) and CHCl$_3$ extraction once;

(e) DNA dialysis in 4 liters of TE buffer, change 3 times; and (f) RNA removal by RNase A treatment and genomic DNA precipitated with 95% ethanol, washed with 70% ethanol, vacuum dried and resuspended in TE buffer.

Restriction enzyme ApoI was diluted by 2-fold serial dilutions. Nine μg genomic DNA was digested partially with varying amounts of ApoI (2, 1, 0.5, 0.25, 0.125, 0.061 units) at 50° C. for 30 min. Good partial digestion was achieved at 0.5, 0.25, and 0.125 units of ApoI. The ApoI partially digested genomic DNA fragments in the range of 3 to 10 kb were gel-purified and ligated to CIP treated pRRS vector with compatible ends. The PRRS vector has been modified by insertion of a BsaI linker at the SspI site. The purpose of this modification was to increase the efficiency of methylase selection. Partial digestions were also carried out with Sau3AI and NlaIII on genomic DNA (2, 1, 0.5, 0.25, 0.125, 0.061 units of Sau3AI; 0.12, 0.06, 0.03, 0.015, 0.0075 units of NlaIII). Again, the DNA fragments in the range of 3 to 10 kb were gel-purified and ligated to BamHI and SphI digested pRRS, respectively. The ligated DNA was used to transform ER2502 electro-competent cells by electroporation. Ap$^R$ transformants were selected on Ap plates (100 μg/ml Ap).

2. Cloning of bsaIMB by Methylase Selection Method

More than 10,000 Ap$^R$ transformants were obtained from ApoI, NlaIII, and Sau3AI libraries. All of the colonies were pooled and amplified in 1 liter LB+Ap overnight culture. Plasmid DNA was prepared by the Qiagen Maxi-prep kit. 0.8 ng-0.2 µg of the library DNA was challenged with 100 units of BsaI at 50° C. for 2 hours. The challenged plasmid DNA was used for re-transformation into ER2502 and plated on Ap plates. Surviving Ap$^R$ transformants were selected. Thirty-six colonies were inoculated into 2 ml LB+Ap and cultured overnight. Plasmid DNA was prepared by Qiagen spin columns and screened for resistance to BsaI digestion. None of the 36 plasmids showed resistance to BsaI digestion.

In order to increase the methylase selection efficiency, after BsaI digestion of plasmid library, the digested plasmids were further treated with 100 units of mung bean nuclease at 37° C. for 1 hour. The mung bean nuclease removed the 4-base overhang and destroyed the AP$^R$ resistant gene (4-base deletion within the β-lactamase gene inactivates this gene). The same plasmid library was challenged with BsaI and split into two half. Half of the DNA was further treated with mung bean nuclease. Both DNA samples were used to transform ER2502 competent cells. It was found that the mung bean nuclease treated DNA gave rise to 5-times less transformants than non-treated DNA. Thirty-six individual transformants from the mung bean nuclease treated DNA were picked and inoculated into 2 ml LB+Ap and cultured overnight. Plasmid DNA was prepared and analyzed by BsaI digestion and agarose gel electrophoresis. Twenty out of 36 screened showed resistance. Isolates #7, #8, #10, #12, and #13 have a common 1.3 kb HindIII fragment by HindIII digestion. This common HindIII fragment was subcloned into pUC19 and sequenced, it was found to encode a C5 methylase. This gene is 1188-bp and was named bsaIMB gene, encoding M.BsaIB. Since BsaI recognition sequence is asymmetric and it was predicted that a second methylase should be present in this R-M system.

3. Inverse PCR Amplification and Sequencing of Adjacent DNA and Identification of bsaIR Gene Since type II R-M genes are usually located in close proximity to each other, efforts were made to amplify the DNA sequence adjacent to bsaIMB gene. *B. stearothermophilus* 6–55 genomic DNA was digested with restriction enzymes with 4 to 6-bp recognition sequence to identify DNA fragments that encompass bsaIMB gene and the flanking DNA. *B. stearothermophilus* genomic DNA was digested with AatII, AseI, BamHI, BssHII, DraI, HaeII, MfeI, NcoI, NdeI, NspI, PstI, SacI, SpeI, SspI, XbaI, and XhoI, respectively. The genomic DNA fragments were self-ligated at a low concentration (2 µg/ml), and the ligated circular molecules were used as the template for inverse PCR. The inverse PCR primers have the following sequence:

```
5' agataaattagctcttacttgagcttc 3'     (SEQ ID NO:7)
                                       (258-98)

5' ggagagcacatataccgaagttag 3'        (SEQ ID NO:8)
                                       (258-99)
```

Inverse PCR conditions were as follows: 94° C. for 30 sec, 55° C. for 30 sec, 72° C. for 3 min, running for 30 cycles with Vent® (exo$^-$) DNA polymerase. A 1.2 kb inverse PCR product was found in the NdeI template. The 1.2 kb fragment was gel-purified and sequenced directly with primers 258–98 and 99, generating approximately 700 bp new DNA sequence.

A second set of inverse PCR primers with the following sequences were synthesized:

```
5' gctcttcagtgtattttgtatctc 3'       (SEQ ID NO:9)
                                       (259-137)

5' tgagaattggattcgaagcactta 3'        (SEQ ID NO:10)
                                       (259-138)
```

AatII, AseI, BamHI, BssHII, DraI, HaeII, MfeI, NcoI, NdeI, NspI, PstI, SacI, SpeI, SspI, XbaI, and XhoI digested and self-ligated DNA molecules were used as the template for inverse PCR. Inverse PCR conditions were as follows: 94° C. for 30 sec, 55° C. for 30 sec. 72° C. for 3 min, running for 30 cycles with Deep Vent® (exo$^-$) DNA polymerase. A 600 bp inverse PCR product was found in the DraI template. The 600 bp fragment was gel-purified and sequenced directly with primers 259–137 and 138, generating approximately 200 bp new DNA sequence.

A third set of inverse PCR primers with the following sequences were synthesized:

```
5' gagatagagtatattgaaatacta 3'        (SEQ ID NO:11)
                                       (259-139)

5' ttacccatggcgggtttgtaatac 3'        (SEQ ID NO:12)
                                       (259-140)
```

AatII, AseI, BamHI, BssHII, DraI, HaeII, MfeI, NcoI, NdeI, NspI, PstI, SacI, SpeI, SspI, XbaI, and XhoI digested and self-ligated DNA molecules were used as the template for inverse PCR. Inverse PCR conditions were as follows: 94° C. for 30 sec, 55° C. for 30 sec, 72° C. for 3 min, running for 30 cycles with Deep Vent® (exo$^-$) DNA polymerase. A 650 bp inverse PCR product was found in AseI template. The 650 bp fragment was gel-purified and sequenced directly with primers 259–139 and 140, generating approximately 400 bp new DNA sequence.

A fourth set of inverse PCR primers with the following sequences were synthesized:

```
5' tctgcagaacaagggcctgggtgg 3'        (SEQ ID NO:13)
                                       (264-210)

5' catattggtcctatttcccttggt 3'        (SEQ ID NO:14)
                                       (264-211)
```

*B. stearothermophilus* genomic DNA was digested with AciI, ApoI, BsaWI, BspHI, BstBI, HincII, HindIII, NlaIII, RsaI, SpeI, SspI, TaqI, TfiI, Tsp45I, and XmnI, respectively. The genomic DNA fragments were self-ligated at a low concentration (2 µg/ml), and the ligated circular molecules were used as the template for inverse PCR. Inverse PCR conditions were as follows: 94° C. for 30 sec. 55° C. for 30 sec, 72° C. for 3 min, running for 30 cycles with Vent® (exo$^-$) DNA polymerase and Taq DNA polymerase, respectively. A 1.2 kb inverse PCR product was found in SspI template. The 1.2 kb fragment was gel-purified and sequenced directly with primers 264–210 and 211, generating approximately 540 bp new DNA sequence.

A fifth set of inverse PCR primers with the following sequences were synthesized:

```
5' caatttaaccaagtatctaaatcg             (SEQ ID NO:15)
                                       (270-223)

5' ttctgtttatattccgagtgaacc            (SEQ ID NO:16)
                                       (270-224)
```

AciI, ApoI, BsaWI, BspHI, BstBI, HincII, HindIII, NlaIII, RsaI, SpeI, SspI, TaqI, TfiI, Tsp45I, and XmnI digested and self-ligated circular molecules were used as the template for inverse PCR. Inverse PCR conditions were as follows: 94° C. for 30 sec, 55° C. for 30 sec. 72° C. for 3 min, running for 30 cycles with Vent® (exo⁻) DNA polymerase. 0.9, 1.6, and 1.2 kb inverse PCR products were found in ApoI, RsaI, and TaqI templates, respectively. The 1.2 kb fragment was gel-purified and sequenced directly with primers 270–223 and 224, generating approximately 600 bp new DNA sequence.

After five rounds of inverse PCR and sequencing of the original methylase positive clones, two additional ORFs were found upstream and downstream. The upstream ORF was named bsaIMA, encoding M.BsaIA, an adenine methyltransferase. Based on the amino acid sequence comparison with other amino-methylases, the M.BsaA methylase belongs to the γ type of N6A methylase.

Among C5 methylases, the conserved amino acid blocks IX and X are located at the C-terminus of the protein. Conserved blocks I to VIII and the variable region are located before blocks IX and X. However, in M.BsaIB, the C5 methylase blocks IX and X are located at the N-terminus, displaying circular permutation of the two blocks. Such circular permutation has been found in the BssHII methylase.

An ORF of 1635 bp was found downstream of the bsaIMA and bsaIMB genes. This ORF was named bsaIR gene. It encodes a 544-aa protein with predicted molecular mass of 63.7 kDa (FIG. 4). As demonstrated below, it is the bona fide R gene, coding for BsaI restriction endonuclease.

4. Cloning of bsmAIM1M2 Genes into pBR322 and Construction of a Pre-Modified Host Since BsmAI recognition sequence (5'GTCTC') overlaps with BsaI recognition sequence (5'GGTCTC3'), M.BsmAI cross-protects *E. coli* chromosome DNA against BsaI digestion. Efforts were made to over-express M.BsmAI first and to construct a pre-modified expression host. M.BsmAI is a fusion of M1 and M2. (BsmAI restriction-modification patent application U.S. Ser. No. 09/957,005 filed Sep. 20, 2001 The patent application for BsmAI restriction-modification is pending in United States.

Two primers were synthesized with the following sequence:

```
                                            (SEQ ID NO:17)
5' GGTGGTGCTAGCGGAGGTAAATAAATGAAAGAAAACACAGAAATTAA
TATAGAT 3' (253-245, underlined nt, NheI site)

(SEQ ID NO:18)
5' GGTGGTGCATGCCTAATATATTTCTTGGTACGTCATTTT 3'
(253-246, underlined nt, SphI site)
```

The bsmAIM gene was amplified from the genomic DNA in PCR using primers 253–245 and 253–246 under PCR condition of 95° C. 1 min, 55° C. 1 min, 72° C. 4 min for 25 cycles. The PCR DNA was purified through a Qiagen spin column and digested with NheI and SphI. The PCR fragment was purified again in low melting agarose gel and ligated to pBR322 with compatible ends. Ligated plasmid was transformed into ER2566 (T7 expression strain, NEB's collection). The $Ap^R$ transformants were pooled and plasmid DNA prepared. The plasmid mixture was challenged with BsmAI endonuclease and retransformed back into ER2566 cells. Four out of six clones were found to have the right size insert and resistant to BsmAI digestion. The pre-modified host ER2566 [pBR322-BsmAIM] was used for expression of the bsaIR gene in *E. coli*.

5. Expression of bsaIR Gene in T7 Expression Vector pACYC-T7ter

To construct a stable expression clone, the bsmAIM gene was expressed from a medium-copy-number vector pBR322 and the bsaIR gene was expressed from a low-copy-number vector pACYC-T7ter. The vector pACYC-T7ter contains a T7 promoter, $Cm^R$ gene, lacI gene, p15A replication origin, and four copies of transcription terminators upstream of T7 promoter to reduce run-off transcription from cryptic *E. coli* promoters.

NdeI and BamHI restriction sites were incorporated into the forward and reverse PCR primers respectively for amplification of bsaIR gene by PCR. The primers have the following sequence:

```
                                            (SEQ ID NO:19)
5' GGTGGTCATATGGGAAAAAAAGCTGAATATGGA 3'
(271-161, underlined nt, NdeI site)

(SEQ ID NO:20)
5'-GGTGGTGGATCCTCATTAATCTAAATCTGCAAATGT 3'
(271-162, underlined nt, BamHI site)
```

The bsaIR gene was amplified by PCR using Vent® DNA polymerase and primers 271–161 and 162 under conditions of 95° C. 1 min, 50° C. 1.5 min, 72° C. 1.5 min for 25 cycles. The PCR product was purified by Qiagen spin column and digested overnight with NdeI and BamHI. After purification from low-melting agarose gel and β-agarase treatment, the DNA was precipitated with ethanol and NaOAc. The PCR DNA was ligated to CIP-treated pACYC-T7ter with compatible ends. The ligated DNA was transformed into pre-modified host ER2566 [pBR322-BsmAIM] and selected for $Ap^R$ $Cm^R$ transformants. Individual transformants were then picked and cultured in 10 ml LB plus Ap (100 μg/ml) and Cm (33 μg/ml) to late log phase and induced with IPTG (0.5 mM final) for 3 h. Thirty-six cell extracts were assayed for BsaI activity. Seven clones (#2, #3, #5, #18, #21, #25, and #32) displayed high BsaI activity. Three plasmids (#2, #3, #5) from highly active clones were sequenced, and #5 were found to contain the wild type sequence and was used in subsequent large-scale purification of BsaI endonuclease protein.

6. Cloning of bsaIMA and bsaIMB Gene into pBR322 to Construct a Pre-Modified Host Two primers were synthesized with the following sequences:

```
                                            (SEQ ID NO:21)
5' GGTGGTGGATCCGGAGGTAAATAAATGAGTAATGCTAAAAGTTTCTC
                                            T3'
(270-148, underlined nt, BamHI site)

(SEQ ID NO:22)
5' GGTGGTGCATGCTTATATTATCGCTAAACTGCTCAA 3'
(270-150, underlined nt, SphI site)
```

The bsaIMA and bsaIMB genes were amplified by Vent® DNA polymerase from genomic DNA in PCR using primers 270–148 and 270–150 under PCR condition of 95° C. 1 min, 55° C. 1.5 min, 72° C. 4 mmin for 25 cycles. The PCR DNA was gel purified through a Qiagen spin column and digested with BamHI and SphI. The PCR fragment was purified again in low melting agarose gel and ligated to pBR322 with compatible ends. Ligated plasmid was transformed into ER2566 (T7 expression strain, NEB's strain collection). The $Ap^R$ transformants were pooled and plasmid DNA prepared. The plasmid mixture was challenged with BsaI endonuclease and retransformed back into ER2566 cells. Plasmid DNA was prepared again and digested with BsaI endonuclease. One out of three clones were found to have the right size insert and resistant to BsaI digestion. The pre-modified host ER2566 [pBR322-BsaIMA&B] was used for expression of the bsaIR gene in *E. coli*.

The plasmid pACYC-T7ter-BsaIR isolated in section 4 was transferred into ER2566 [pBR322-BsaIMA&B] by transformation. Ap$^R$ and Cm$^R$ colonies were selected and transformants were grown in 10 ml LB plus Ap and Cm overnight. The 10 ml cells were inoculated into 500 ml LB plus Ap and Cm and cultured for five hours. Following addition of 0.5 mM IPTG (final concentration) cell growth was continued for 3 h. Cells were harvested and resuspended in a sonication buffer. Cell lysis was completed by sonication and cell debris was removed by centrifugation. Cell extract was diluted and assayed on T7 DNA. The recombinant BsaI yield from this expression clone was estimated at 0.7–1.4×10$^6$ units BsaI/g of wet cell. The recombinant BsaI activity from the previous expression strain ER2566 [pBR322-BsmAIM1M2, pACYC-T7ter-BsaIR] was 1.0–2.0×10$^6$ units of BsaI/g of wet cell. A third expression strain was also constructed in which the bsaIMA and bsaIMB genes were expressed from pACYC184 and the bsaIR gene was expressed from pUC19. This strain also generated less BsaI units per gram of wet cells. Therefore, the strain ER2556 [pBR322-BsmAIM1M2, pACYC-T7ter-BsaI] was used as the BsaI production strain.

7. Purification of BsaI Endonuclease

Figure 6:
FIG. 6 Purified recombinant BsaI endonuclease protein on SDS-PAG gel. Lane 1, broad range protein size marker; lane 2, purified recombinant BsaI endonuclease. BsaI endonuclease apparent size=61 kDa; Predicted size=63.7 kDa.

Cell extract was prepared by sonication of 4 grams of IPTG-induced cells resuspended in 20 ml sonication buffer (50 mM Tris-HCl, pH 7.8, 10 mM β-mercaptoethanol). Cell debris was removed by centrifugation at 15 k rpm for 30 min. The BsaI activity was measured. The cell extract was heated at 55° C. for one hour to denature *E. coli* thermolabile proteins. Denatured proteins were removed by centrifugation. The supernatant was loaded onto a 20 ml Heparin Sepharose column. Following extensive washing with low salt buffer (20 mM Tris-HCl, pH 7.5, 50 mM NaCl, 10 mM β-mercaptoethanol, 0.1 mM EDTA), fractions were eluted with a NaCl gradient of 0.05 M-1 M. Fractions containing BsaI endonuclease as determined by an activity assay on λ DNA were pooled and dialyzed overnight in DEAE-Sepharose loading buffer (20 mM Tris-HCl, pH 7.5, 50 mM NaCl, 10 mM β-mercaptoethanol, 0.1 mM EDTA). After dialysis, the protein mixture was loaded onto a DEAE Sepharose column equilibrated with the same buffer. Fractions were eluted with a 0.05 M–1 M NaCl gradient and those fractions containing purified BsaI were pooled. The recombinant BsaI was analyzed on SDS-PAGE. It was estimated to be >92% homogeneity (FIG. 6). A total of 10$^6$ units of functionally purified BsaI were obtained. The apparent molecular size of BsaI protein on the gel appeared to be 61 kDa, slightly smaller than the predicted size of 63.7 kDa. To determine the exact start amino acid of the recombinant BsaI endonuclease, the purified protein was subjected to N-terminal sequencing analysis. It was confirmed that the protein contained the correct N-terminal amino acid sequence:

(M) GKKAEYGQGHPIFLEYAEQ (SEQ ID NO:23).

The migration difference may arise from factors such as the aa residue composition and side chain charges.

The strain ER2566 [pBR322-BsmAIM, pACYC-T7ter-BsaIR] has been deposited under the terms and conditions of the Budapest Treaty with the American Type Culture Collection on Mar. 26, 2002 and received ATCC Accession No. PTA-4181.

What is claimed is:

1. Isolated DNA coding for the BsaI restriction endonuclease, wherein the isolated DNA is obtainable from *Bacillus stearothermophilus* 6–55.

2. A recombinant DNA vector comprising a vector into which a DNA segment encoding the BsaI restriction endonuclease gene has been inserted.

3. Isolated DNA encoding the BsaI restriction endonuclease wherein the isolated DNA is obtainable from ATCC No. PTA-4181.

4. A vector that comprise the isolated DNA of claim 3.

5. A host cell transformed by the vector of claims 2 or 4.

6. A method of producing recombinant BsaI restriction endonuclease comprising culturing a host cell transformed with the vector of claims 2 or 4 under conditions suitable for expression of said endonuclease and methylase.

* * * * *